(12) United States Patent
Huitema

(10) Patent No.: US 6,638,297 B1
(45) Date of Patent: Oct. 28, 2003

(54) SURGICAL STAPLE

(75) Inventor: Thomas W. Huitema, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/158,118

(22) Filed: May 30, 2002

(51) Int. Cl.$^7$ .............................................. A61B 17/064
(52) U.S. Cl. ...................................... 606/219; 606/213
(58) Field of Search ................................ 606/213, 215, 606/219, 220

(56) References Cited

U.S. PATENT DOCUMENTS

| | | |
|---|---|---|
| 2,797,275 A | 6/1957 | Seeger |
| 4,485,816 A | 12/1984 | Krumme |
| 4,719,917 A * | 1/1988 | Barrows et al. ............ 606/220 |
| 5,002,563 A | 3/1991 | Pyka et al. |
| 5,171,252 A | 12/1992 | Friendland |
| 5,258,009 A * | 11/1993 | Conners ..................... 180/445 |
| 5,342,395 A * | 8/1994 | Jarrett et al. ................ 606/219 |
| 5,342,396 A * | 8/1994 | Cook ......................... 606/219 |
| 5,350,400 A * | 9/1994 | Esposito et al. ............ 606/219 |
| 5,366,458 A | 11/1994 | Korthoff et al. |
| 5,395,381 A | 3/1995 | Green et al. |
| 5,441,509 A | 8/1995 | Vidal et al. |
| 5,673,840 A | 10/1997 | Schulze et al. |
| 5,709,704 A | 1/1998 | Nott et al. |
| 5,772,105 A | 6/1998 | Zadno-Azizi et al. |
| 5,817,113 A | 10/1998 | Gifford, III et al. |
| 6,193,733 B1 | 2/2001 | Adams |
| 6,198,974 B1 | 3/2001 | Webster, Jr. |
| 6,325,085 B1 | 12/2001 | Gower |
| 6,329,069 B1 | 12/2001 | Azizi et al. |
| 6,461,453 B1 * | 10/2002 | Abrams et al. ............ 148/402 |

FOREIGN PATENT DOCUMENTS

| | | |
|---|---|---|
| JP | Hei 7-18357 A61 B | 1/1995 |
| WO | WO96/16603 A1 | 6/1996 |
| WO | WO00/07506 A2 | 2/2000 |
| WO | WO00/57796 A1 | 5/2000 |
| WO | WO01/11097 A1 | 2/2001 |
| WO | WO01/45571 A1 | 6/2001 |

OTHER PUBLICATIONS

Published: by Wayman, C.M. and Duerig, T.W. "An Introduction to Martensite and Shape Memory".
NDC, Nitinol Devices & Components: http://www.nitinol.com/2prof.htm; p. 1.
NDC, Nitinol Devices & Components: http://www.nitinol.com/3tech.htm; pp. 1–3.

* cited by examiner

Primary Examiner—David O. Reip
(74) Attorney, Agent, or Firm—Dean Garner

(57) ABSTRACT

In accordance with the present invention, there is provided a surgical staple having first undeployed shape for loading into a stapler, and a second deployed shape for connecting tissue together. The staple has a crown and first and second legs, one attached to each end of the crown. The legs extend from the crown in a direction substantially perpendicular to the longitudinal axis of the crown when the staple is in its first shape. The legs comprise first and second layers of material joined together. The first layer of material is a superelastic alloy having a relaxed configuration substantially in the staple's second shape. The second layer of material is a linear elastic material having a relaxed configuration substantially in the staple's first shape. The second layer of material has sufficient rigidity to keep the first layer in the first shape prior to the staple being deployed.

14 Claims, 3 Drawing Sheets

SURGICAL STAPLE

FIELD OF THE INVENTION

The present invention has application in conventional endoscopic and open surgical instrumentation as well application in robotic-assisted surgery. The present invention has even further relation to surgical staples and staplers.

BACKGROUND OF THE INVENTION

In recent years surgery has markedly advanced through the performance of laparoscopic and endoscopic surgical procedures such as cholecystectomies, gastrostomies, appendectomies, and hernia repair. These procedures are accomplished through a trocar assembly, which is a surgical instrument used to puncture a body cavity. The trocar contains a sharpened obturator tip and a trocar tube or cannula. The trocar cannula is inserted into the skin to access the body cavity, by using the obturator tip to penetrate the skin. After penetration, the obturator is removed and the trocar cannula remains in the body. It is through this cannula that surgical instruments are placed. Specifically, it is through this trocar cannula that surgical stapling instruments with cutting mechanisms are placed. One such trocar is the Endopath ® trocar manufactured by ETHICON ENDO-SURGERY, Cincinnati, Ohio.

The application of endoscopic surgical stapling and suturing instruments has been provided in such surgical procedures. One such endoscopic instrument, often referred to as an endocutter, is capable severing tissue and providing hemostasis along both sides of the cut. An example of an endocutter can be found in U.S. Pat. No. 5,673,840 issued on Oct. 7, 1997, which is hereby incorporated herein by reference.

In the case of such an endocutter, the tissue is compressed between a lower jaw and an anvil. The lower jaw holds a cartridge that holds tiny drivers that house U-shaped staples. After the tissue is compressed, axial movement of the firing wedges forces the drivers and staples radially toward the anvil. This movement causes the staples to pierce the compressed tissue and strike curved pockets in the face of the anvil. When the legs of the staples strike the anvil pockets, they buckle from column loading and curl inward in a manner similar in concept to operation of a common office stapler. The anvil pocket geometry causes them to deform inward, forming a B-like shape as the legs of the staples are permanently deformed back on themselves. Often, two triple rows of staples are being simultaneously formed, with a knife following just behind the forming operation to separate the tissue between the two triple rows (lines) of staples. There are a number of problems associated with the forces required to deform the staples and the shape the deformed staple assumes under certain circumstances. The high forces require expensive materials and manufacturing techniques because the jaw and anvil need to be highly strong and rigid. In addition, the high forces require high firing wedge forces. These forces must be generated over the length of the staple line. The resulting total energy input limits the length of staple lines that can be formed by a human using a single hand squeezing motion. Many physicians find it difficult to fire an endocutter.

Furthermore, it is difficult to use a single staple size that can provide hemostasis over a range of tissue thicknesses. With conventional metal staples, the staple legs tend to simply buckle part of the way back from the distal ends. This distal portion remains primarily straight. As a result, when the staples are deformed most extensively for very thin tissue, the straight portions of the staple legs pass beyond the flat base of the staple and the sharp points end up protruding out of the tissue where they can catch and lacerate tissue. If the tissue is very thick and only the distal portions of the staple legs are formed, the staple legs won't curve back on themselves to form the hook-like geometry required to hold the tissue in place.

SUMMARY OF THE INVENTION

In accordance with the present invention, there is provided a surgical staple having first undeployed shape for loading into a stapler, and a second deployed shape for connecting tissue together. The staple has a crown and first and second legs, one attached to each end of the crown. The legs extend from the crown in a direction substantially perpendicular to the longitudinal axis of the crown when the staple is in its first shape. The legs comprise first and second layers of material joined together. The first layer of material is a superelastic alloy having a relaxed configuration substantially in the staple's second shape. The second layer of material is a linear elastic material having a relaxed configuration substantially in the staple's first shape. The second layer of material has sufficient rigidity to keep the first layer in the first shape prior to the staple being deployed.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
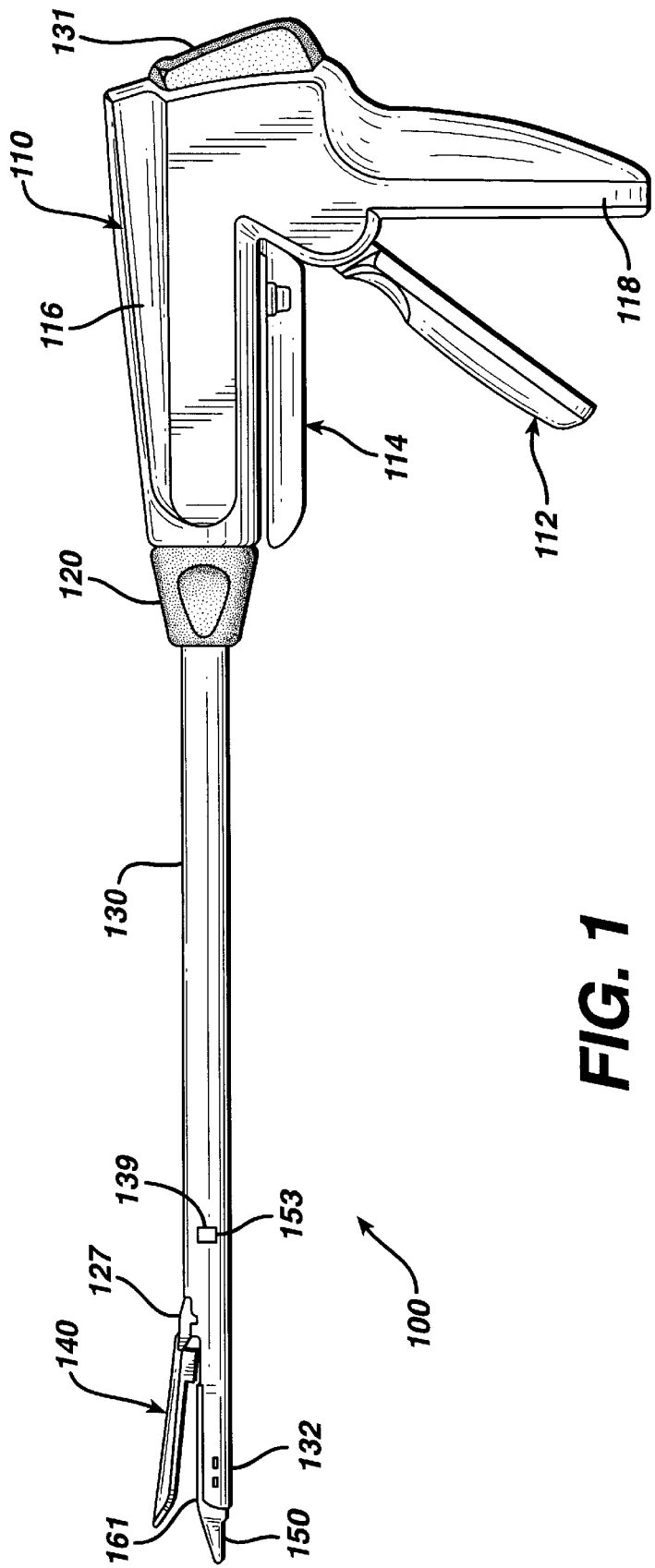
FIG. 1 is a side view of a surgical stapler, which can be used with the present invention.

Referring now to the drawings wherein like numerals indicate the same elements throughout the views, there is shown in FIG. 1 a surgical stapler, or endocutter, 100 designed to be used with the present invention. Stapler 100 is of the kind described in the hereinbefore incorporated U.S. Pat. No. 5,673,840. Stapler 100 which contains a handle portion 110, rotating means 120, a shaft portion 130, anvil portion 140, and cartridge assembly 150. A knife means (not shown) is slidable within the cartridge assembly 150 to cut tissue. In the handle portion 110 there is a first or closure trigger (also called a clamping trigger) 112, and second or firing trigger 114. The clamping trigger 112 causes the anvil portion 140 to come into proximity of the cartridge assembly 150. The firing trigger 114 causes staples to eject from the cartridge and form against the anvil 142. Trigger 114 also causes the knife means to move through the cartridge assembly 150, in order to cut tissue.

As will be appreciated by those skilled in the art, the below described surgical staple has equal application for use in open linear cutters, such as those described in U.S. Pat. No. 4,520,817 issued to Green on Jun. 4, 1985, which is hereby incorporated herein by reference. In addition, as used herein staple refers to any type of substantially rigid and deformable surgical fasteners. Consequently, as will be appreciated by those skilled in the art, the below described staple has equal application for use in a clip applier or ligation device, such as the one described in U.S. Pat. No. 5,447,513 issued to Davison et al. on Sep. 5, 1995, which is hereby incorporated herein by reference.

Figure 2:
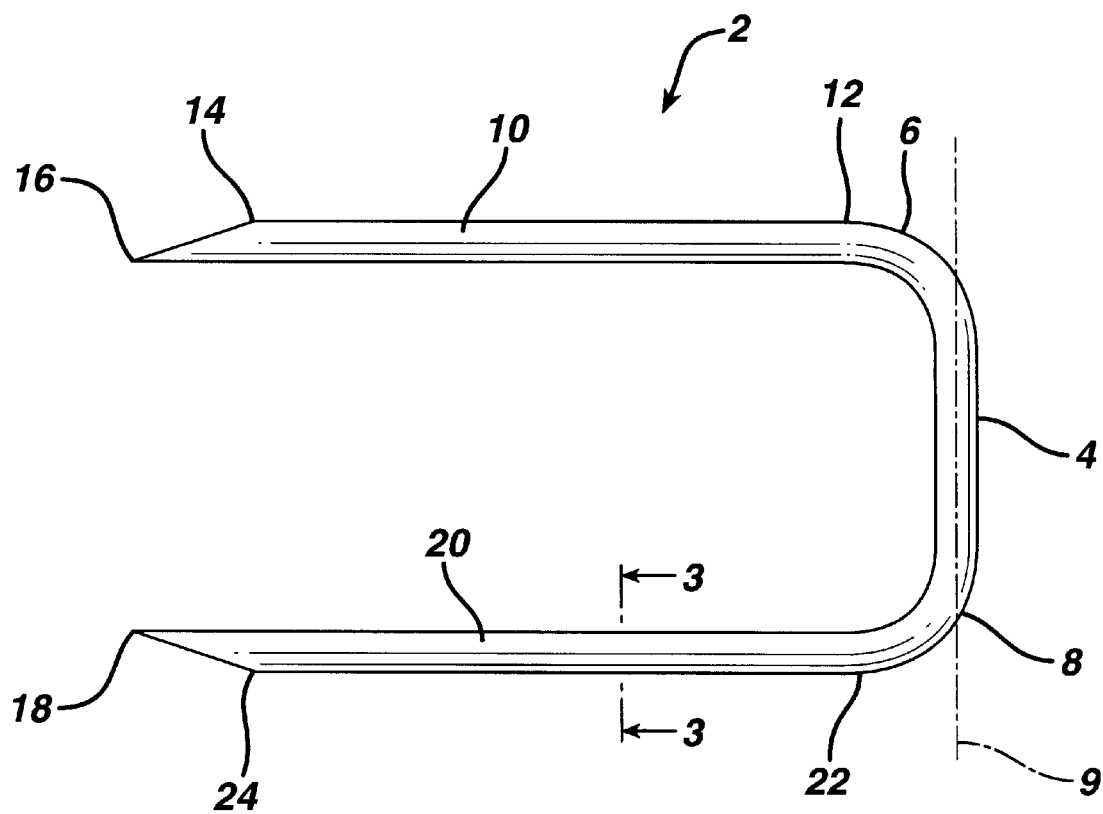
FIG. 2 is a plan view of a surgical staple made in accordance with the present invention and showing the staple in its undeployed shape.

Referring now to FIG. 2, there is shown a surgical fastener, which in this embodiment is shown as staple 2 made in accordance with the present invention, and designed to be loaded in a cartridge of the type described above as item 150. As will be discussed below, staple 2 has a first undeployed shape, and a second deployed shape. FIG. 2GP depicts staple 2 in its first undeployed shape. Staple 2 has a crown 4 having first and second ends 6 and 8 and a longitudinal axis 9 extending therebetween. Staple 2 also includes first and second legs 10 and 20. Legs 10 and 20 have first ends 12 and 22 which are attached to first and second ends 6 and 8 of crown 4. Legs 10 and 20 also have second ends 14 and 24 which extend from crown 4 in a direction generally perpendicular to longitudinal axis 9. Second ends 14 and 24 may include sharpened tips 16 and 18.

Figure 3:
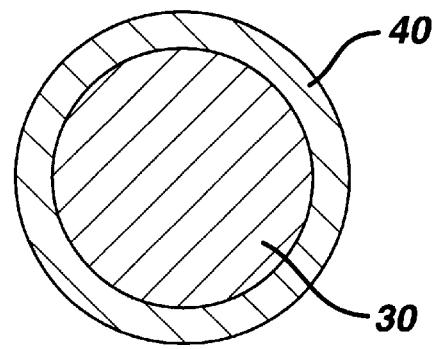
FIG. 3 is a cross sectional view of the staple shown in FIG. 2, taken along line 3—3.

The material construction of staple 2 can best be described by referring to FIG. 3. As seen from the drawing, at least the legs, if not the entire staple, is formed from 2 coextensive layers of material 30 and 40 joined together. As will be discussed in greater detail below, the first layer of material, or core, 30 is made from a superelastic alloy having a relaxed configuration substantially in the staple's second shape. The second layer of material 40, or shell, is made from a linear elastic material having a relaxed configuration substantially in the staples first shape first shape. The second layer of material 40 has sufficient rigidity to keep the first layer in the first shape prior to the staple being deployed.

For purposes of this invention, the first and second layers of material are interchangeable. For example the first inner layer 30, or core, could be made from the linear elastic material, while the second outer layer 40, or shell is constructed from a superelastic material. Moreover, it is not necessary that the layers have circular cross-sections, but could take on any desired shape. In addition, it is not necessary that the cross section of the staple have the core/shell configuration. The layers could be juxtaposed and coextensive with each other, or have any other desired configuration.

The first layer 30 of material is preferably made from a superelastic or pseudoelastic alloy. One such type of material is commonly referred to as Nitinol. The nature of the superelastic transformations of shape memory alloys is discussed in "Engineering Aspects of Shape Memory Alloys", T W Duerig et al, on page 370, Butterworth-Heinemann (1990). Subject matter disclosed in that document is incorporated in this specification by this reference to the document. A principal characteristic of shape memory alloys involves an initial increase in strain, approximately linearly with stress. This behavior is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys", on page 376.

Non-linear superelastic properties can be introduced in a shape memory alloy by a process which involves cold working the alloy for example by a process that involves pressing, swaging or drawing. The superelastic properties are employed by the staple in its change of configuration between its first or undeployed/restrained shape, and its second or deployed/relaxed shape. An appropriate treatment can involve a combination of cold working (for example by swaging, drawing or, in particular by mandrel expansion) and heat treatment at a temperature that is less than the recrystallisation temperature of the alloy while the staple is constrained in the configuration resulting from the cold work. A plurality of the cold work and heat treatment steps can be used. The staple can then be deformed towards undeployed shape, the deformation being recoverable, substantially elastically. In this way, deformations of up to 8% strain can be imparted and recovered substantially elastically. The alloy for the first layer 30 is preferably manufactured such that it exhibits superelastic properties at body temperature.

Preferable Nitinol or Ni-Ti binary alloys for the first layer of material have a nickel content of at least about 50 atomic percent (hereinafter at. %), preferably at least about 50.5 at. %. The nickel content will usually be less than about 54 at. %, preferably less than about 52 at. %. As will be appreciated by those skilled in the art, the first layer can be made from other Ni-Ti based alloys, including alloys with ternary and quaternary additions. Examples of elements that can be incorporated in the alloy include Fe, Co, Cr, Al, Cu and V. Added elements can be present in amounts up to about 10 at. %, preferably up to about 5 at. %. Preferably the austenite finish temperature (Af) is below body temperature, and more preferably is around 0° C.

The second layer of material 40 is preferably made from a linear elastic material, such as iron, non-superelastic Nitinol, stainless steel or titanium. The second layer could also be made from a material, which would impart radiopaque qualities to the staple so it could be seen better under x-ray. The yield strength of the second layer of material is set to be modestly higher than the recovery strength of the first layer of material For example purposes, the manufacturing of the staple will now be described, wherein the second layer 40 comprises iron. The staple can be initially manufactured by co-drawing a tube of iron wire around a Nitinol wire until you have a wire having the cross-section shown in FIG. 3. That is the wire can be formed by sliding a length of Nitinol wire inside a length of iron tubing and then drawing the two together until the desired diameter of wire is produced. The diameter of the Nitinol core, the wall thickness of the iron cover, and the level of work hardening in the cover can be varied to create staples with varying degrees of biased-properties.

The wire can then be cut into a desired staple size length segments. Thereafter the segment is cooled so that the Nitinol is substantially martensitic, and then the segment is deformed into its desired second/deployed shape, shown in FIG. 4. The segment is then heat treated to shape set the Nitinol and partially stress relieve the Titanium. After the Nitinol in the wire had been shape-set, the staple could be straightened to the geometry depicted in FIG. 2 to form staple 2 which will then be loaded into and used in conventional surgical staplers.

The staple 2 combines shape-memory and linear-elastic materials such that the staple has some of the properties of shape-memory materials and some of the properties of linear-elastic materials. When deploying the staple, such as ejecting it from a cartridge onto an anvil, the sum of applied stresses and internally generated shape-memory recovery stresses exceed the yield strength of the linear-elastic material such that the staple will deform. When the loads are applied in such a fashion that they aid the shape-set material recovery stresses and the external load required to cause deformation will be lower than if the forces were applied to the linear-elastic portion of the staple alone.

Figure 4:
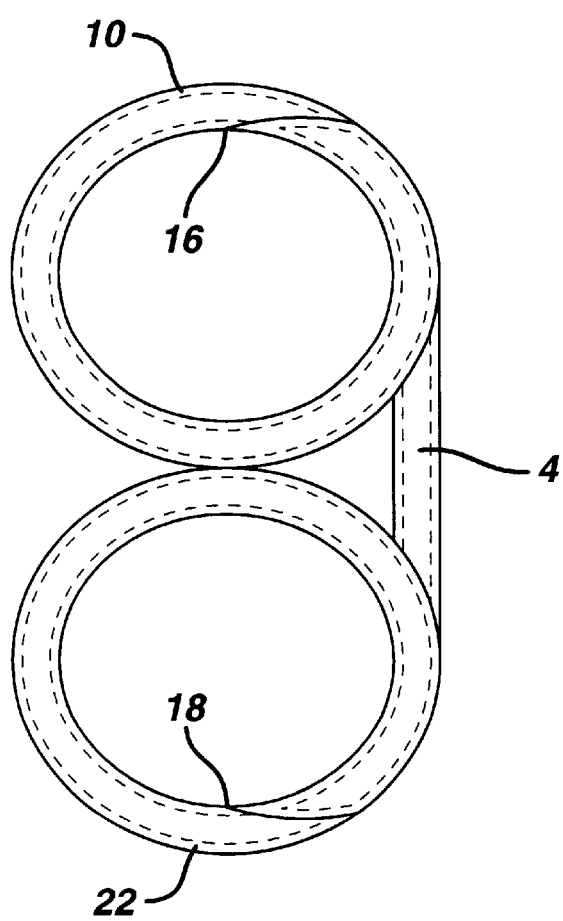
FIG. 4 is a plan view of the surgical staple shown in FIG. 2, but showing the staple in its deployed shape.

As the staple is deployed, the staple would begin deforming and assuming the desired "B" shape at much lower loads than a conventional staple. This means that even at early stages of staple formation, the tips of the staple would take on a hook-like shape and eventually bend back upon themselves as shown in FIG. 4. In contrast, a conventional staple would initially buckle closer to the middle of the staple and a major distal portion of the staple leg might stay straight and not even bend. As a result, when the staples are deformed most extensively for very thin tissue, the straight portions of the staple legs pass beyond the flat base of the staple and the sharp points end up protruding out of the tissue where they can catch and lacerate tissue. If the tissue is very thick and only the distal portions of the staple legs are formed, the staple legs won't curve back on themselves to form the hook-like geometry required to hold the tissue in place. The above mentioned staple and its associated geometry reduce these drawbacks.

Radial forming forces would remain lower for the above described staple throughout the forming process providing the staples were originally formed and shape-set at a formed height slightly less than the stapler could stroke to form them, even in thin tissue. This fundamental reduction in staple forming forces would have a ripple effect throughout the instrument because the tendency to force the anvil and cartridge channel apart would be reduced. Smaller, lighter components could be used for a given combination of staples lines and staple line length. In addition, it would make it feasible to design cantilevered-jaw staplers (the most common configuration) with longer staple line lengths than are currently feasible without making the components objectionably large and bulky.

The properties of the above mentioned staple could cause a manufacturer to increase the number of staples, and consequently the staple line length, that could be formed by a human using a single hand squeezing motion. This means the single-stroke, one-handed firing mechanism popular and economical on smaller staplers could be used on staplers with longer staple lines. This would provide a distinct advantage over the cost and complexity of staplers requiring multiple actuations to form all the staplers or relying on powered designs that deprive the surgeon of tactile feedback during use.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. A medical fastener having first undeployed shape for loading into a stapler, and a second deployed shape for connecting tissue together, said fastener comprising:
   a. a crown having two ends and a longitudinal axis extending therebetween, first and second legs one attached to each end of said crown, wherein said legs extend from said crown in a direction substantially perpendicular to said longitudinal axis of said crown when said fastener is in said first shape; and
   b. wherein said legs comprise first and second layers of material joined together, said first layer of material comprising a superelastic alloy treated so as to have an Af temperature below 37° C. and a relaxed configuration substantially in said second shape, said second layer of material comprising a linear elastic material having a relaxed configuration substantially in said first shape and having sufficient rigidity to keep said first layer in said first shape prior to said fastener being deployed.

2. The fastener of claim 1 wherein said second layer comprises a material selected from at least one of the following materials: iron, non-superelastic nickel titanium alloy, stainless steel, titanium.

3. The fastener of claim 1 wherein said first layer comprises a nickel titanium alloy.

4. The fastener of claim 3 wherein said first layer has an Af temperature below 0° C.

5. The fastener of claim 3 wherein said second layer of material is disposed concentrically around said first layer.

6. The fastener of claim 5 wherein said legs have a substantially circular cross-section.

7. The fastener of claim 1 wherein said second shape is substantially a B-shape.

8. A surgical staple having first undeployed shape for loading into a stapler, and a second deployed shape for connecting tissue together, said staple comprising:
   a. a crown having two ends and a longitudinal axis extending therebetween, first and second legs one attached to each end of said crown, wherein said legs extend from said crown in a direction substantially perpendicular to said longitudinal axis of said crown when said staple is in said first shape, said legs having distal end which are sharp; and
   b. wherein said legs comprise first and second layers of material joined together, said first layer of material comprising a superelastic alloy treated so as to have an Af temperature below 37° C. and a relaxed configuration substantially in said second shape, said second layer of material comprising a linear elastic material having a relaxed configuration substantially in said first shape and having sufficient rigidity to keep said first layer in said first shape prior to said staple being deployed.

9. The staple of claim 8 wherein said second layer comprises a material selected from at least one of the following materials: iron, non-superelastic nickel titanium alloy, stainless steel, titanium.

10. The staple of claim 8 wherein said first layer comprises a nickel titanium alloy.

11. The staple of claim 10 wherein said first layer has an Af temperature below 0° C.

12. The staple of claim 10 wherein said second layer of material is disposed concentrically around said first layer.

13. The staple of claim 12 wherein said legs have a substantially circular cross-section.

14. The staple of claim 8 wherein said second shape is substantially a B-shape.

* * * * *